(12) United States Patent
Hirano et al.

(10) Patent No.: US 6,375,949 B1
(45) Date of Patent: Apr. 23, 2002

(54) MONOCLONAL ANTIBODY RECOGNIZING SERUM AMYLOID A

(75) Inventors: Norihito Hirano; Michiko Yamada, both of Tochigi (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/029,345

(22) PCT Filed: Aug. 22, 1996

(86) PCT No.: PCT/JP96/02342

§ 371 Date: Jun. 9, 1998

§ 102(e) Date: Jun. 9, 1998

(87) PCT Pub. No.: WO97/08335

PCT Pub. Date: Mar. 6, 1997

(30) Foreign Application Priority Data

Aug. 30, 1995 (JP) .............................................. 7-246695

(51) Int. Cl.⁷ ............................................ A61K 39/395
(52) U.S. Cl. ...................... 424/145.1; 435/7.1; 436/518; 436/536; 436/541; 530/388.25
(58) Field of Search ..................... 530/388.25; 436/536, 436/541, 518; 424/145.1; 435/7.1

(56) References Cited

PUBLICATIONS

Supplementary European Search Report dated Nov. 9, 1998.
Wilkins, J. et al. "Rapid Automated Enzyme Immunoassay of Serum Amiloid A" Clin.Chem. (1994) pp. 1284–1290.
*The Journal of Clinical Investigation*, G. Husby et al., 53, pp. 1054–1064 (1974).
Rinshokensa, Toshiyuki Yamada et al., 32 (2), pp. 167–172 (1988).
*Journal of Immunological Methods*, Thomas L. McDonald et al., 144, pp. 149–155 (1991).
*Clinical Chemistry*, Julie Wilkins et al., 40 (7), pp. 1284–1290 (1994).
*American Chemical Society*, Francis E. Dwulet et al., pp. 1677–1682 (1988).
*Ann Clin Biochem.*, Toshiyuki Yamada et al., 30, pp. 72–76 (1993).
*Journal of Immunological Methods*, Ernst Malle et al., 182, pp. 131–144 (1995).
Cruse et al. Illustrated Dictionary of Immunology CRC Press pp. 8–9, 1995.*

* cited by examiner

*Primary Examiner*—Patrick Nolan
(74) *Attorney, Agent, or Firm*—Gilberto M. Villacorte; Pepper Hamilton LLP

(57) ABSTRACT

The present invention provides a monoclonal antibody useful for immunoassay of human serum amyoloid A (SAA), which can be used as a marker for inflammations based on the agglutination reaction, as well as a reagent for immunoassay comprising the monoclonal antibody, and a method for immunoassay utilizing the monoclonal antibody. In a preferred embodiment, the monoclonal antibody recognizes at least one epitope of human amyloid A and it agglutinates with human serum amyloid A. The present invention improves the specificity of immunoassay by utilizing the agglutination reaction of SAA and monoclonal antibody in the presence or absence of other monoclonal antibodies recognizing SAA.

12 Claims, 4 Drawing Sheets

| CLONE | 3 | 6 | 7 | 14 | 15 | 16 | 17 | 18 | 20 | 21 | 22 | 25 | 27 |
|---|---|---|---|---|---|---|---|---|---|---|---|---|---|
| 3 | 170 | 103 | 102 | 82 | 63 | 112 | 124 | 185 | 78 | 98 | 90 | 104 | 50 |
| 6 | 103 | 0 | 0 | 13 | 73 | 4 | 38 | 296 | 99 | 108 | 2 | 4 | 52 |
| 7 | 102 | 0 | 1 | 1 | 108 | 5 | 61 | 279 | 122 | 162 | 8 | 8 | 142 |
| 14 | 82 | 13 | 1 | 4 | 199 | 1 | 53 | 395 | 177 | 184 | 6 | 10 | 171 |
| 15 | 63 | 73 | 108 | 199 | 58 | 56 | 3662 | 254 | 83 | 125 | 115 | 79 | 43 |
| 16 | 112 | 4 | 5 | 1 | 56 | 4 | 40 | 232 | 80 | 101 | 6 | 5 | 51 |
| 17 | 124 | 38 | 61 | 53 | 3662 | 40 | 75 | 2179 | 2195 | 1377 | 39 | 42 | 2986 |
| 18 | 185 | 296 | 279 | 395 | 254 | 232 | 2179 | 688 | 265 | 306 | 286 | 282 | 220 |
| 20 | 78 | 99 | 122 | 177 | 83 | 80 | 2195 | 265 | 246 | 128 | 115 | 140 | 101 |
| 21 | 98 | 108 | 162 | 184 | 125 | 101 | 1377 | 306 | 115 | 220 | 125 | 117 | 93 |
| 22 | 90 | 2 | 8 | 6 | 115 | 6 | 39 | 286 | 140 | 125 | 4 | 3 | 114 |
| 25 | 104 | 4 | 8 | 10 | 79 | 5 | 42 | 282 | 101 | 117 | 3 | 2 | 101 |
| 27 | 50 | 52 | 142 | 171 | 43 | 51 | 2986 | 220 | 74 | 93 | 114 | 101 | 48 |

FIG. 1

RSFFSFLGEA FDGARDMWRA YSDMREANY I GSDK YFHARG

NYDAAKRGPG GVWAAEAISD ARENIQRFFG HGAEDSLADQ

AANEWGRSGK DPNHDRPAGL PEKY

SEQUENCE LISTING

<160> NUMBER OF SEQ ID NOS: 1

<210> SEQ ID NO 1
<211> LENGTH: 104
<212> TYPE: PRT
<213> ORGANISM: Homo sapiens

<400> SEQUENCE: 1

```
Arg Ser Phe Phe Ser Phe Leu Gly Glu Ala Phe Asp Gly Ala Arg Asp
 1               5                  10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
 65                  70                  75                  80

Ala Ala Asn Glu Trp Gly Arg Ser Gly Lys Asp Pro Asn His Asp Arg
            85                  90                  95

Pro Ala Gly Leu Pro Glu Lys Tyr
            100
```

MONOCLONAL ANTIBODY RECOGNIZING SERUM AMYLOID A

TECHNICAL FIELD

The present invention relates to a monoclonal antibody recognizing amyloid A in human serum (hereinafter abbreviated as SAA) and cause the agglutination reaction, a reagent for immunoassay comprising the monoclonal antibody, and a method for immunoassay using the monoclonal antibody.

BACKGROUND ART

In such fields as clinical examinations, immunoassay is often utilized in order to measure certain substances simply and conveniently or with high sensitivity and specificity. Antibodies are required for immunoassay. Monoclonal antibodies are indispensable tools for immunoassay because of their numerous advantages: that they can be continuously supplied with uniform characteristics; that an amount of antigens used can be small since the antibody-producing cells can be established as cell lines; and among others, that antibodies of high specificity can be easily obtained. Monoclonal antibodies are important tools not only for assay but also for purification of substances and for studies on their physiological activities and in vivo behavior.

SAA is a serum protein with a molecular weight of about 12,000, which is considered as a precursor protein of amyloid protein A (hereinafter abbreviated as AA protein) that is deposited in tissues in a certain type of amyloidosis (J. Clin. Invest. 53: 1054–1061, 1974). Recently, it was reported that the serum SAA value rises in inflammatory disorders, and therefore it has been recognized as a sensitive marker for inflammations (Rinshokensa 32: 2, p 168, 1988).

There are some reports on the monoclonal antibodies recognizing SAA (J. Immunol. Methods 144, 149–155, 1991; Clin. Chem. 40/7, 1284–1290, 1994). In these reports, ELISA is constituted with the monoclonal antibodies recognizing SAA.

Generally speaking, those monoclonal antibodies that are sufficiently usable in ELISA often are not practically useful in the agglutination method. This is because the antibody to be used must have the following characteristics in either case of utilizing carrier particles like latex or of not requiring a carrier as in the case of immunological turbidimetric analysis.

First of all, the agglutination method requires higher affinity. Compared to ELISA, it requires generally a higher level of affinity in order to achieve the agglutination reaction and to maintain a physically stable aggregate. Especially with monoclonal antibodies, one would need to prepare those with high affinities because the reaction needs to be constituted solely with the antibody molecules that react specifically with certain epitopes. However, conventional monoclonal antibodies cannot satisfy this requirement. If one attempts to constitute a reaction system with a monoclonal antibody with insufficient affinity, it is impossible to conduct measurement by the agglutination method because the antibody does not form an aggregate that can be analyzed with practical sensitivity. If the quantity of the antibody is increased to compensate for the low affinity, sufficient sensitivity cannot be obtained since the number of antibody molecules that can bind to one antigen molecule does not change. The measure to increase the quantity of the antibody is also unsatisfactory when using carriers such as latex by binding it to the antibody because the amount of the antibody bound is limited.

Furthermore, the agglutination reaction requires multiple existence of the epitope recognized by the monoclonal antibody on a single antigen and positional relationship among the epitope at multiple sites must be suitable for agglutination. Therefore, the positional relationship, which is not an issue in ELISA, may become an obstacle in the agglutination method. Although the same condition is required in the sandwich ELISA method, it is disadvantageous to rely solely on the contiguous epitopes even if their physical sites are different because, as described earlier, the agglutination method requires a physically stronger binding. This is because steric hindrance tends to occur, which makes it difficult to obtain a large, stable aggregate. Thus, also from the standpoint of epitope selection, conventional monoclonal antibodies are not suitable for the agglutination method.

An object of the present invention is to provide a novel monoclonal antibody that enables measurement of SAA based on the agglutination reaction. Another object of the invention is to provide a novel reagent for immunoassay comprising the monoclonal antibody, and a novel method for immunoassay using the monoclonal antibody.

DISCLOSURE OF THE INVENTION

Using highly purified SAA and enhancing the antigenicity of SAA by combining SAA with various adjuvant components to make it into a unique form of immunogen, the present inventors have obtained several kinds of hybridomas producing the monoclonal antibodies recognizing human SAA with the following reactivity characteristics: (1) that they recognize the epitope of human serum amyloid A, and (2) that they agglutinate by reacting with human serum amyloid A in the absence/presence of other monoclonal antibodies, to isolate several monoclonal antibodies from the hybridomas. The present inventors also conducted agglutination experiments of SAA using the monoclonal antibodies, and have established a novel method for immunoassay utilizing the monoclonal antibodies, thereby completing the invention.

The monoclonal antibodies of the present invention enable immunoassay by the agglutination reaction. The use of currently available monoclonal antibodies against SAA has been limited to such measurement methods as ELISA because they have insufficient affinities for the agglutination reaction. Since the monoclonal antibodies of the present invention have new characteristics that they agglutinate by reacting with SAA, it is possible to provide a convenient method for measuring SAA based on the agglutination reaction.

The monoclonal antibodies of the present invention can be obtained by immunizing mice, rats, etc. with the purified SAA, and immortalizing the antibody-producing cells by some means. As to the techniques for immortalization, known techniques include cell fusion with tumor cells such as myelomas and transformation with Epstein-Barr virus.

When preparing hybridomas by cell fusion, the myeloma cells from the same animal species as the immunized animal may be used, or they can originate from some other animals, thereby creating hetero-hybridoma cells. SAA is a protein also found in serum of non-human animals, and it increases by immunization as a stimulus. Consequently it is advantageous to use an animal species that does not show such a phenomenon, e.g., rats, as the animal to be immunized because the antibody titer is likely to rise.

SAA to be utilized as the immunogen can be obtained by purification using a known method. Specifically, SAA can be recovered as a pure protein by obtaining a high density lipoprotein (hereinafter abbreviated as HDL) fraction from crude serum by ultracentrifugation, subjecting it to delipidation, and purifying by means of, e.g., ion exchange chromatography. It is desirable to use such highly purified protein in order to obtain the cells that produce monoclonal antibodies specific to SAA in a high yield. Although there is a report that the unpurified HDL fraction obtained through ultracentrifugation was used as an immunogen, the antibody-producing cells obtained using such immunogens often produce antibodies recognizing various apolipoprotein antigens, which may be disadvantageous in terms of, e.g., cloning.

When using purified SAA as an immunogen, a variety of techniques can be applied to enhance its antigenicity. Freund's complete adjuvant (hereinafter abbreviated as FCA) is one of the necessary components to enhance immunogenicity. It is also effective to use the SAA adsorbed to lipid liposomes to serve as an immunogen. It is pointed out that SAA exhibits poor antigenicity in the immunized animals since SAA is a protein inherently found in many mammals' blood. One of the reasons why there is no report on the monoclonal antibody usable in the agglutination reaction is presumed to be this low antigenicity of SAA, and therefore it is important to enhance the antigenicity in order to obtain the monoclonal antibody of the present invention. An adjuvant component useful in obtaining the monoclonal antibody of the present invention is exemplified by FCA supplemented with cells of tubercle bacilli. FCA originally contains tubercle bacilli, but better results can be expected by reinforcing this component. An intramuscular injection of the pertussis vaccine at the time of immunization can also be expected to enhance the immunization effects.

In the present invention, agglutination reaction of the monoclonal antibody in response to SAA can be confirmed through the following method. The simplest method may be to allow the monoclonal antibody and SAA to react under a favorable condition for the immune reaction and to confirm the agglutination ability by observing as an indicator as to whether the immune complex precipitation forms. By this method, however, it is generally difficult to perform a quantitative observation without using a sensitizing agent or the like.

It is preferable to use the latex agglutination reaction in order to quantitatively measure agglutination ability of the monoclonal antibody. An example of the method for confirming the agglutination ability of the monoclonal antibody by the latex agglutination reaction is described below.

The anti-SAA monoclonal antibody is physically adsorbed to polystyrene latex (average particle diameter 0.109 µm) at 37° C. for 1 hour, and then suspended in a dispersion medium (0.1 M HEPES buffer, pH 7.4, containing 1% BSA) to give the final latex concentration of 1%, resulting in a monoclonal antibody-sensitized latex emulsion. This emulsion is reacted with a sample having a certain SAA concentration, and the resulting agglutination is optically measured. Known optical measurement methods include the method of measuring changes in absorbance and changes in light scattering.

The following is an example of the measurement of absorbance changes using the Immunological Latex Agglutination Reaction Measurement System LA-2000 (trade name, manufactured by EIKEN KAGAKU-Analytical Instrument). The measurement parameters are shown below. With these parameters, the absorbance changes over 400 seconds after the initiation of reaction are calculated as DOS. DOS is a specific value to LA-2000.

| | |
|---|---|
| SAA concentration: | 31.5 µg/ml |
| Sample volume: | 20 µl |
| Emulsion volume: | 300 µl |
| Absorbance measurement: | 400 seconds |

Under these reaction conditions, 0.1 M HEPES buffer (pH 7.4) alone is measured in order to determine the optical fluctuation of the instrument itself. Then, as a blank test, the same buffer is used as a sample to obtain the reagent blank. The basic value (lower limit) is calculated by adding, to the reagent blank average, its doubled standard deviation and further the instrument fluctuation range (reagent blank+2 SD+instrument's fluctuation range). Occurrence of agglutination can be judged when a measured value is larger than the basic value. Similar test methods can be performed using a general spectrophotometer, without using specialized systems such as LA-2000.

The monoclonal antibodies of the present invention include those that react with SAA by themselves to cause agglutination, and those that react with SAA in the presence of various anti-SAA monoclonal antibodies to cause agglutination. Moreover, among those that react with SAA by themselves to cause the agglutination reaction, there are the antibodies that exhibit a stronger agglutination in the presence of various anti-SAA monoclonal antibodies than that attainable when they are used individually.

For example, the following data were obtained by measuring the binding affinities of the monoclonal antibodies shown in FIG. 1. Since there were no notable correlation between the affinity constant and the intensity of agglutination activity, it seemed impossible to simply infer the strength of agglutination activity of the monoclonal antibody to SAA based on its affinity.

Clone 15: $8.4 \times 10^{-7}$
Clone 16: $2.0 \times 10^{-8}$
Clone 17: $1.0 \times 10^{-7}$
Clone 18: $8.5 \times 10^{-7}$ Furthermore, while the monoclonal antibodies, which was actually obtained by the present inventors, recognized the regions shown, for example in FIG. 4, as epitopes, there were no correlation between the epitopes and the agglutination activities. The epitopes shown in FIG. 4 were obtained by analyzing the representative monoclonal antibodies among those described in FIG. 1. Therefore, it seems difficult to predict the agglutination activity of the monoclonal antibodies recognizing SAA based solely on the epitopes. The names of amino acids are herein abbreviated as follows.

| | |
|---|---|
| Alanine: | A or Ala |
| Arginine: | R or Arg |
| Asparagine: | N or Asn |
| Aspartic acid: | D or Asp |
| Cyctaine: | C or Cys |
| Glutamine: | Q or Gln |
| Glutamic acid: | E or Glu |
| Glycine: | G or Gly |
| Histidine: | H or His |
| Isoleucine: | I or Ile |
| Leucine: | L or Leu |
| Lysine: | K or Lys |
| Methionine: | M or Met |
| Phenylalanine: | F or Phe |
| Proline: | P or Pro |

-continued

| | |
|---|---|
| Serine: | S or Ser |
| Threonine: | T or Thr |
| Tryptophan: | W or Trp |
| Tyrosine: | Y or Tyr |
| Valine: | V or Val |

The hybridomas SAA-17 and SAA-21, obtained by the present inventors and included in the present invention, have been respectively deposited under the following conditions.
Deposit concerning hybridoma SAA-17:
(A) Name and address of depositary institution
   Name: National Institute of Bioscience and Human Technology, Agency of Industrial Science and Technology, Ministry of International Trade and Industry
   Address: 1-3 Higashi 1-chome, Tsukuba-shi, Ibaragi, Japan (postal code 305)
(B) Date of deposit (Original date of deposit) Aug. 2, 1995
(C) Accession number FERM BP-5616
Deposit concerning hybridoma SAA-21:
(A) Name and address of depositary institution
   Name: National Institute of Bioscience and Human Technology, Agency of Industrial Science and Technology, Ministry of International Trade and Industry
   Address: 1-3 Higashi 1-chome, Tsukuba-shi, Ibaragi, Japan (postal code 305)
(B) Date of deposit (Original date of deposit) Aug. 2, 1995
(C) Accession number FERM BP-5617

These hybridomas are rat-mouse heterohybridomas established by fusing the antibody-producing cells derived from the rat, which was immunized using the method described above, with the mouse myeloma cells. These hybridomas can be injected into the abdominal cavity of nude mice to recover the ascites and to purify the monoclonal antibodies. They can also be cultured in an appropriate medium to obtain the culture supernatant and to purify the monoclonal antibodies.

The monoclonal antibodies of the present invention exhibit differences in agglutination characteristics, as described earlier, depending on the combination when plural antibodies are used. Therefore, when utilizing these monoclonal antibodies as reagents, one should empirically choose appropriate combinations to readily achieve the expected sensitivity and the range of measurement. The number of monoclonal antibodies to be combined is not limited to two, but larger numbers of monoclonal antibodies can be combined. An aggregate that exhibits more stable and stronger binding can be expected to be formed when three or more different kinds of monoclonal antibodies are used in combination. Alternatively, it is also possible to control the agglutination intensity or the quantifiable range by manipulating the combination and the mixing ratio.

When the reagent of the present invention is prepared by coupling plural monoclonal antibodies to the carrier particles, it can be prepared by either the method of mixing after each species of monoclonal antibody is coupled to the carrier particle or the method of coupling the mixture of plural monoclonal antibodies. The former method may be advantageous because one can accommodate the subtle differences in binding conditions among different clones and it is easy to adjust the mixing ratio of antibodies.

As the reagent for immunoassay of the present invention, the monoclonal antibody can be used in a free state or as coupled to an insoluble carrier. Preferable insoluble carriers include particulate carriers made of synthetic organic materials such as latex, and inorganic materials such as silica, alumina, gold colloid, or the like. In order to couple the monoclonal antibody to these particulate carriers, chemical bonding or physical adsorption may be utilized.

The monoclonal antibodies that constitute the reagents of the present invention can be utilized as fragments resulted from digestion with appropriate enzymes for the purpose of suppressing non-specific influences of the rheumatoid factor and complements. Known antibody fragments include $F(ab')_2$ given by pepsin digestion, Fab by papain digestion, and Facb' by plasmin digestion.

It is possible to combine known ingredients other than those mentioned above with the reagent for immunoassay of SAA according to the present invention. Such ingredients include buffers that provide necessary pH for immune reactions, reaction enhancers that promote immune reactions, reaction stabilizers or blockers that suppress non-specific reactions, and preservatives such as sodium azide that improve preservability of the reagent.

Among the buffers applicable in the present invention, GOOD's buffers are particularly preferred because they not only provide the advantageous pH for immune reactions but also have minimum influence on proteins. Followings are used as GOOD's buffers.

2-(N-Morpholino)ethanesulfonic acid (abbreviated as MES)
Piperazine-N,N'-bis(2-ethane sulfonic acid) (abbreviated as PIPES)
N-(2-Acetamido)-2-aminoethanesulfonic acid (abbreviated as ACES)
N,N-bis(2-hydroxyethyl)-2-aminoethanesulfonic acid (abbreviated as BES)
Bis(2-hydoxyethyl)iminotris(hydroxymethyl)methane (abbreviated as Bis-Tris)
3-[N,N-Bis(2-hydroxyethyl)amino]-2-hydroxypropanesulfonic acid (abbreviated as DISPO)
N-2-Hydroxyethylpiperazine-N'-3-propanesulfonic acid (abbreviated as EPPS)
N-2-Hydroxyethylpiperazine-N'-2-ethanesulfonic acid (abbreviated as HEPES)
N-2-Hydroxyethylpiperazine-N'-2-hydroxypropane-3-sulfonic acid (abbreviated as HEPPSO)
3-(N-Morpholino)propanesulfonic acid (abbreviated as MOPS)
3-(N-Morpholino)-2-hydroxypropanesulfonic acid (abbreviated as MOPSO)
Piperazine-N,N'-bis(2-hydroxypropanesulfonic acid) (abbreviated as POPSO)
N-Tris(hydroxymethyl)methyl-3-aminopropanesulfonic acid (abbreviated as TAPS)
N-Tris(hydroxymethyl)methyl-2-hydroxy-3-aminopropanesulfonic acid (abbreviated as TAPSO)
N-Tris(hydroxymethyl)methyl-2-aminoethanesulfonic acid (abbreviated as TES)
Other buffers, such as the following, may also be used.
2-Amino-2-hydroxymethyl-1,3-propanediol, also called Tris(hydroxymethyl)aminomethane
Phosphate buffers
Ammonium buffers The reaction enhancers include polyethyleneglycol and dextran sulfate. The reaction stabilizers and blockers usable in the present invention include BSA (bovine serum albumin), animal sera, IgG, IgG fragments (Fab or Fc), albumins, milk proteins, amino acids, poly-amino acids, choline, polysaccharides such as sucrose, gelatin, decomposition products of gelatin, casein, and polyhydric alcohols such as glycerol, which are effective for stabilizing the reaction or suppressing nonspecific reactions during the immune reaction.

The reagent for immunoassay of SAA of the present invention, which may include the various components as mentioned above, can be provided as solutions or in a dry state. In providing them as solutions, materials such as surfactants, carbohydrates, and inactive proteins can be further added in order to enhance the stability of the proteins. These stabilizing agents are also effective as stabilizers or vehicles when the reagents are dried.

The immunoassay of SAA according to the present invention are performed using the reagent for immunoassay comprising the monoclonal antibodies of the present invention as described above. The immunoassay can be carried out by adding the reagents to the sample and monitoring the progress of the agglutination reaction optically or with the naked eyes.

BRIEF DESCRIPTIONS OF THE DRAWINGS

FIG. 1 is the measured values of agglutination obtained using an emulsion prepared by mixing equal quantities of two different monoclonal antibodies.

Figure 4:
Figure 4:
Figure 4:
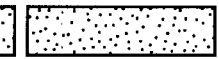
Figure 4:
Figure 4:
Figure 4:
Figure 4:
Figure 2:
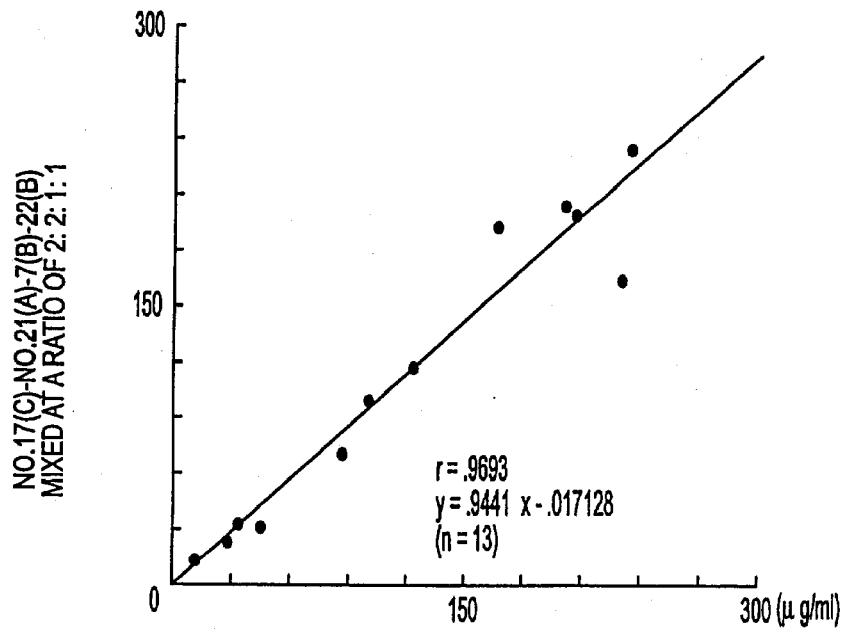
Figure 3:
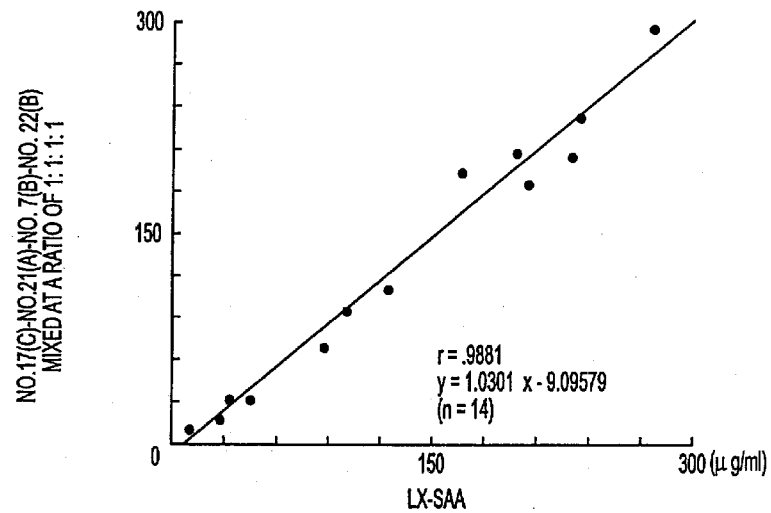
Figure 4:
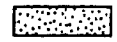
Figure 4:
Figure 4:
Figure 4:
Figure 4:
Figure 4:

FIG. 4 shows the mapping of epitopes recognized by the monoclonal antibodies of FIG. 1 (SEQ. ID. NO: 4) over the amino acid sequence of SAA.

BEST MODE FOR CARRYING OUT THE INVENTION

Examples of the present invention are illustrated below, but are not construed to limit the scope of the present invention.

1. Preparation of the SAA Immunogen

The high-SAA serum (100 $\mu$g/ml) 1 L was used as a starting material. By ultracentrifugation, the upper layer of density 1.23 and then the bottom layer of density 1.063 were recovered, delipidated with methanol/ether (1:3) under cooling, applied to a Sephadex G-200 column (equilibrated with a 0.01 M Tris-HCl buffer, pH 8.6, containing 6 M urea and 0.5% Tween 20), and further applied to a cyanogen bromide-activated Sepharose-4B column (Pharmacia) to which an anti-Apo A I antibody, an anti-Apo C III antibody, and an anti-human serum albumin antibody had been bound by a conventional method to remove contaminating proteins. Thus, 30 mg of purified SAA was obtained from 1 L of serum. The purified SAA showed a single band at the position of M.W. 12,000 by SDS-PAGE, and did not react with other Apolipoprotein antibodies. Moreover, its amino acid sequence was, from the N-terminus, Ser Phe Phe Ser Phe Leu Gly Glu Ala Phe Asp Gly Ala Arg Asp Met Trp Arg Ala Tyr, and through the data base search it was found to be identical to form II and IV lacking the N-terminal Arg, which was reported by Dwulet et al. (Biochem. 27: p 1677, 1988).

2. Monoclonal Antibodies

[2-1] Immunization of Rats

The FCA supplemented with the purified SAA 100 $\mu$g/animal from 1 above and human tubercle bacilli 4 mg/ml were made into an emulsion by a usual method and used to immunize 9-week-old female WKAH/HKm rats. At the same time, 100 $\mu$l/animal of alum precipitated trivalent diphtheria tetanus toxoid pertussis vaccine (Takeda Pharmaceuticals) was intramuscularly injected into the left hind leg of the animal.

Every three weeks thereafter, an emulsion prepared with SAA 50 $\mu$g/animal and FCA by a usual method was intraperitoneally injected as an immunogen, and the blood was withdrawn periodically to measure the antigen titer by ELISA. The ELISA protocol is shown below.

[2-2] ELISA of SAA Antibodies

ELISA was used to measure the antibody titer and to confirm antigen-specific antibody activities. For blocking, conjugate dilution, and serum dilution, a 20 mM phosphate buffer containing 0.15 M NaCl supplemented with 1% BSA (pH 7.2, hereinafter abbreviated as BSA-PBS) was used.

The purified SAA was dissolved in a 20 mM phosphate buffer (pH 7.2, hereinafter abbreviated as PBS) to give the concentration of 10 $\mu$g/ml, dispensed into the wells of 60-well Terasaki plates (SUMITOMO Bakelite Medical, MS-31600) at 10 $\mu$l/well, followed by sensitization at 37° C. 2 hours. After washing with PBS, 1% BSA-PBS was added at 10 $\mu$l/well, blocked at 37° C. for 2 hours, and kept at 4° C.

After the plate was washed once with PBS, a 10 $\mu$l sample whose antibody activity was to be examined was put onto the Terasaki plate and incubated at 37° C. for 30 minutes. The plate was washed three times with PBS, supplemented with 10 $\mu$l of a commercially available anti-rat IgG-POD conjugate (Cappel) which had been diluted 10,000 fold with 1% BSA-PBS, and incubated at 37° C. for 30 minutes. After the plate was washed three times with PBS, 10 $\mu$l of the substrate solution containing OPD and hydrogen peroxide were added thereto and the plate was incubated at 37° C. for 30 minutes to measure color development. The same procedure was repeated using 10 $\mu$l each of 1% BSA-PBS as a negative control, and a $10^2$ dilution of the immunized rat serum as a positive control, in place of the sample above.

[2-3] Cell Fusion and Cloning

After it was confirmed that the antibody titer had risen to $10^4$ by ELISA, 50 $\mu$g of SAA dissolved in the physiological saline was intraperitoneally injected, and the spleen was taken out three days later. Spleen cells were harvested and washed with the RPMI1640 medium, and fused with the X-63-Ag 8-653 mouse myeloma cells by the polyethylene glycol (hereinafter abbreviated as PEG) method. The condition for the cell fusion is as follows. The cells were aliquoted into centrifuge tubes at a ratio of spleen cells:myeloma cells=3:1, to which 50% PEG solution 1 ml was added, and 50 ml of the warmed RPMI1640 was further added slowly to dilute the PEG. Next, the PEG was removed by centrifugation, and the cells were dispersed in the HAT medium at $7.1 \times 10^5$ spleen cells/well, which were then plated onto 96-well plates.

After the HAT selection, colonies were observed in most of the wells. The culture supernatant from each well was screened by ELISA using the POD-labeled anti-rat IgG antibody, and the cells from 30 wells that had developed color were cloned by 3 to 4 times of the limiting dilution method. Ultimately, the 13 clones that produce IgG class monoclonal antibodies that react with SAA were established. Although it was difficult to consistently establish such many clones by the conventional immunization methods such as the methods using mice or using rats, the immunization method used at this time was able to simultaneously produce many clones. These 13 clones were used in the following confirmation of reactivity.

3. Preparation of Reagents using the Monoclonal Antibodies

Each of the 13 hybridoma clones obtained in 2 above was inoculated into the abdominal cavity of PRISTANE-treated nude mice (BALB/c-nu), and the ascites was collected two weeks later. The ascites was centrifuged (3,000 rpm, 5 minutes), and the monoclonal antibody was precipitated from the supernatant by ammonium sulfate fractionation. The precipitate was recovered, dissolved in PBS, and dialyzed against the same PBS, yielding the anti-SAA monoclonal antibody (10 mg/ml). Subclasses of the monoclonal antibodies used are as follows. The subclass was determined by Ouchterlony's method between the anti-rat subclass antisera, (Bethyl) and the culture supernatants.

Clone 3: IgG2a
Clone 6: IgG2b
Clone 7: IgG2a
Clone 14: IgG2c
Clone 15: IgG2a
Clone 16: IgG2a
Clone 17: IgG1
Clone 18: IgG2a
Clone 20: IgG2a
Clone 21: IgG2a
Clone 22: IgG2a
Clone 25: IgG2a
Clone 27: IgG2a Each anti-SAA monoclonal antibody was physically adsorbed to polystyrene latex (average particle diameter 0.109 μm) at 37° C. for 1 hour, and then suspended in a dispersion medium (0.1 M HEPES buffer, pH 7.4, containing 1% BSA) to the final latex concentration of 1%, producing 13 types of SAA-latex agglutination reaction reagents (hereinafter simply referred to as emulsions).

4. Reactivity of the Monoclonal Antibody

The emulsions obtained in 3 above were used either individually or in pairs containing an equal quantity of two kinds, to prepare a total of 91 types of reagents, and the occurrence of agglutination was observed by allowing them to react with SAA. The agglutination reaction was confirmed by the absorbance analysis using the Immunological Latex Agglutination Reaction Measurement System LA-2000 (trade name, manufactured by EIKEN KAGAKU-Analytical Instrument). The measurement conditions are as follows. Under these conditions, the difference in absorbance over the 400 seconds after the initiation of reaction is calculated as DOS. The value is specific to LA-2000. The results are shown in FIG. 1.

| | |
|---|---|
| SAA concentration: | 31.5 μg/ml |
| Sample volume: | 20 μl |
| Emulsion volume: | 300 μl |
| Absorbance measurement: | 400 sec |

The DOS of each combination is shown in FIG. 1. The value for the reaction involving a single clone (appearing on a diagonal) is encircled by a dotted line, and the value is italicized for the particular combination when it is more than 10% higher than the sum of half the DOS for single-component emulsions (i.e., when the agglutination is enhanced by mixing). From these results, it was confirmed that antibodies that exhibit agglutination even by themselves (such as Clone 17 and 21) could be obtained. It was also observed numerous combinations which show stronger agglutination than used individually when two different monoclonal antibodies are combined (i.e., the emulsions are mixed). Among the combinations that enhance agglutination, there were some antibodies that do not agglutinate alone, or some that exhibit extremely strong agglutination ability when combined with specific antibodies. For example, Clone 7 exhibits strong agglutination ability when combined with Clone 3 or Clone 21, and so does Clone 21 with Clone 17. The combination that showed especially strong agglutination is encircled by the solid line.

On the other hand, there were many cases in which the agglutination became weak by the mixing compared with the use of individual antibodies (underlined in FIG. 1), which indicates that merely combining multiple monoclonal antibodies does not necessarily result in enhancement of agglutination.

The presence or absence of agglutination ability was determined by the following indexes. First, a 0.1 M HEPES buffer (pH 7.4) alone was measured in order to determine the optical fluctuation of the instrument itself (20). Then as a blank test, the same buffer is used as a sample to obtain the reagent blank (−11 to +10). The basic value is calculated by adding, to the reagent blank average (0.93), its standard deviation (2.93) multiplied by 2 and further the instrument fluctuation range (reagent blank+2 SD+instrument's fluctuation range). Occurrence of agglutination was judged when a measured value is larger than the basic value. In this experiment, this value was 27. Therefore, the ones showing values over 27 in FIG. 1 can be considered as forming agglutination.

5. Combinations of Multiple Monoclonal Antibodies

Figure 2:
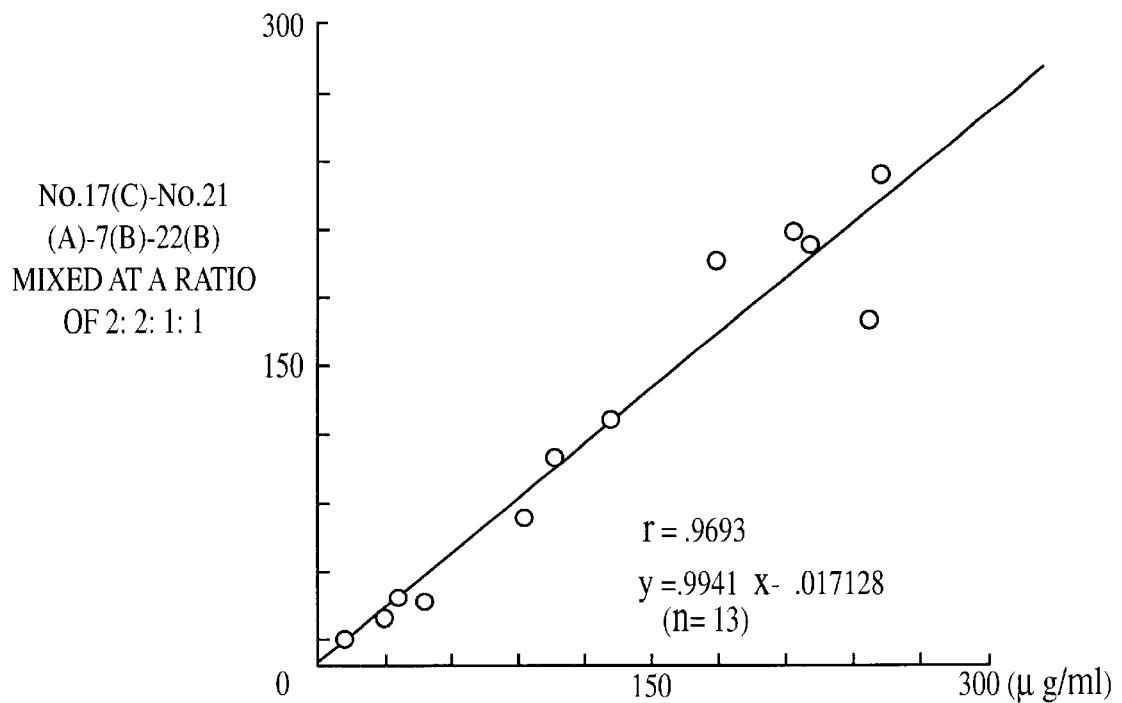
FIG. 2 shows the correlation between the measured values of agglutination obtained using an emulsion prepared by mixing plural species of monoclonal antibodies ($\mu$g/ml, ordinate) and those obtained using an emulsion prepared with polyclonal antibodies ($\mu$g/ml, abscissa).
Figure 3:
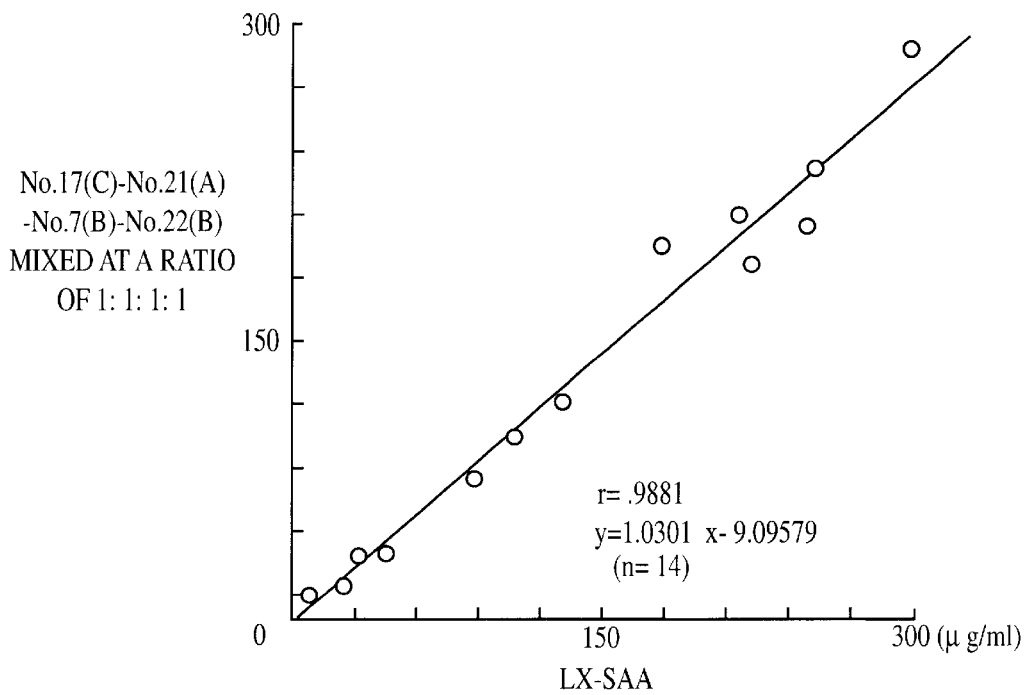
FIG. 3 shows the correlation between the measured values of agglutination obtained. using an emulsion prepared by mixing plural species of monoclonal antibodies ($\mu$g/ml, ordinate) and those obtained using an emulsion prepared with polyclonal antibodies ($\mu$g/ml, abscissa).

With reference to the pair-wise combination results obtained in 4 above, the combinations of three or more kinds were also examined for agglutination activities. Among the clones whose data are shown in FIG. 1, monoclonal antibodies 7, 17, 21, and 22 were individually made into emulsions, which were mixed at different ratios to produce reagents for the agglutination reaction of SAA containing multiple species of monoclonal antibodies. Using the resulting emulsions containing multiple monoclonal antibodies, various concentrations of SAA-containing serum samples were examined by the same procedure used in 4 above. The correlation between the above values and those obtained using the known latex agglutination reaction reagent for measuring SAA (Ann. Clin. Biochem. 30: 72–76, 1993), which was prepared with polyclonal antibodies, was examined. The results are shown in FIGS. 2 and 3.

As shown in the figures, the combinations of monoclonal antibodies used in these examples all exhibited high degrees of correlation to the values obtained with polyclonal antibodies. Thus, the monoclonal antibodies of the present invention can provide the reagents for immunoassay having agglutination activity comparable to polyclonal antibodies, while retaining the high specificity of the monoclonal antibody. Among the several combinations of monoclonal antibodies shown, the highest degree of correlation to the values obtained with polyclonal antibodies was observed in the case of the combination of 17:21:7:22≈1:1:1:1 (FIG. 2).

Industrial Applicability

The present invention provides novel monoclonal antibodies, which improves the specificity of immunoassay utilizing the agglutination reaction of SAA and achieves stabilization of quality of the reagents. Namely, the use of monoclonal antibodies is enabled in the immunoassay based on the agglutination reaction of SAA though the assay has so far had to depend on polyclonal antibodies that have poor specificity and are difficult to maintain uniform quality.

What is claimed is:

1. A monoclonal antibody recognizing human serum amyloid A, wherein said monoclonal antibody recognizes at least one epitope of human serum amyloid A and it agglutinates with human serum amyloid A in the absence of other monoclonal antibodies recognizing human serum amyloid A, wherein said monoclonal antibody is produced by hybridoma SAA-17 (Accession No. FERM BP-5616).

2. A monoclonal antibody recognizing human serum amyloid A, wherein said monoclonal antibody recognizes at least one epitope of human serum amyloid A and it agglutinates with human serum amyloid A in the absence of other monoclonal antibodies recognizing human serum amyloid A, wherein said monoclonal antibody is produced by hybridoma SAA-21 (Accession No. FERM BP-5617).

3. A reagent for the immunoassay of human serum amyloid A, comprising a monoclonal antibody recognizing human serum amyloid A, wherein said monoclonal antibody recognizes at least one epitope of human serum amyloid A and it agglutinates with human serum amyloid A in the absence of other monoclonal antibodies recognizing human serum amyloid A, wherein said monoclonal antibody is produced by at least one of hybridoma SAA-17 (Accession No. FERM BP-5616) or hybridoma SAA-21 (Accession No. FERM BP-5617).

4. The reagent of claim 3, wherein said monoclonal antibody is coupled to an insoluble carrier.

5. The reagent of claim 4, wherein said insoluble carrier is a particulate carrier.

6. The reagent of claim 3, wherein said reagent is provided in a liquid state.

7. The reagent of claim 3, wherein said reagent further comprises surfactants, reaction enhancers, reaction stabilizers, reaction blockers, or a combination thereof.

8. A method for the immunoassay of human serum amyloid A which comprises reacting human serum amyloid A with one or more monoclonal antibodies comprising.
   (a) recognizing at least one epitope of human serum amyloid A, and
   (b) agglutinating with human serum amyloid A in the absence of other monoclonal antibodies wherein said monoclonal antibody is produced by at least one of hybridoma SAA-17 (Accession No. FERM BP-5616) or hybridoma SAA-21 (Accession No. FERM BP-5617).

9. The method of claim 8, wherein said monoclonal antibody is coupled to a particulate carrier and agglutination is based on the reaction between the antibody and human serum amyloid A, wherein said agglutination is measured optically.

10. The method of claim 8, wherein immunoprecipitates resulting from the reaction between said monoclonal antibody and human serum amyloid A are measured optically.

11. The method of claim 8, wherein said monoclonal antibody is prepared by coupling at least one monoclonal antibody to a multiplicity of carrier particles.

12. The method of claim 8, wherein said monoclonal antibody is prepared by either mixing after coupling the carrier particles with the monoclonal antibody or mixing before coupling the carrier particles with the monoclonal antibody.

* * * * *

UNITED STATES PATENT AND TRADEMARK OFFICE
CERTIFICATE OF CORRECTION

PATENT NO. : 6,375,949 B1
DATED : April 23, 2002
INVENTOR(S) : Hirano et al.

It is certified that error appears in the above-identified patent and that said Letters Patent is hereby corrected as shown below:

Drawings,
Substitute Figures 1- 4 with the attached figures.

Column 12,
Line 37, delete "." and insert -- : --

Signed and Sealed this

Twenty-fourth Day of December, 2002

JAMES E. ROGAN
*Director of the United States Patent and Trademark Office*

| CLONE | 3 | 6 | 7 | 14 | 15 | 16 | 17 | 18 | 20 | 21 | 22 | 25 | 27 |
|---|---|---|---|---|---|---|---|---|---|---|---|---|---|
| 3 | 170 | 103 | 102 | 82 | 63 | 112 | 124 | 185 | 78 | 98 | 90 | 104 | 50 |
| 6 | 103 | 0 | 0 | 13 | 73 | 4 | 38 | 296 | 99 | 108 | 2 | 4 | 52 |
| 7 | 102 | 0 | 1 | 1 | 108 | 5 | 61 | 279 | 122 | 162 | 8 | 8 | 142 |
| 14 | 82 | 13 | 1 | 4 | 199 | 1 | 53 | 395 | 177 | 184 | 6 | 10 | 171 |
| 15 | 63 | 73 | 108 | 199 | 58 | 56 | 3662 | 254 | 83 | 125 | 115 | 79 | 43 |
| 16 | 112 | 4 | 5 | 1 | 56 | 4 | 40 | 232 | 80 | 101 | 6 | 5 | 51 |
| 17 | 124 | 38 | 61 | 53 | 3662 | 40 | 75 | 2179 | 2195 | 1377 | 39 | 42 | 2986 |
| 18 | 185 | 296 | 279 | 395 | 254 | 232 | 2179 | 688 | 265 | 306 | 286 | 282 | 220 |
| 20 | 78 | 99 | 122 | 177 | 83 | 80 | 2195 | 246 | 128 | 115 | 140 | 101 | 74 |
| 21 | 98 | 108 | 162 | 184 | 125 | 101 | 1377 | 306 | 115 | 220 | 125 | 117 | 93 |
| 22 | 90 | 2 | 8 | 6 | 115 | 6 | 39 | 286 | 140 | 125 | 4 | 3 | 114 |
| 25 | 104 | 4 | 8 | 10 | 79 | 5 | 42 | 282 | 101 | 117 | 3 | 2 | 101 |
| 27 | 50 | 52 | 142 | 171 | 43 | 51 | 2986 | 220 | 74 | 93 | 114 | 101 | 48 |

FIG. 1

RSFFSFLGEA FDGARDMWRA YSDMREANYI GSDKYFHARG

NYDAAKRGPG GVWAAEAISD ARENIQRFFG HGAEDSLADQ

AANEWGRSGK DPNHDRPAGL PEKY